United States Patent [19]

Ohmura et al.

[11] Patent Number: 5,521,287

[45] Date of Patent: *May 28, 1996

[54] RECOMBINANT HUMAN SERUM ALBUMIN, PROCESS FOR PRODUCING THE SAME AND PHARMACEUTICAL PREPARATION CONTAINING THE SAME

[75] Inventors: Takao Ohmura; Akinori Sumi; Wataru Ohtani; Naoto Furuhata; Kazuya Takeshima; Kaeko Kamide; Munehiro Noda, all of Osaka; Masahide Kondo; Syoichi Ishikawa, both of Kyoto; Kazuhiro Oohara, Osaka; Kazumasa Yokoyama, Osaka; Nagatoshi Fujiwara, Osaka, all of Japan

[*] Notice: The term of this patent shall not extend beyond the expiration date of Pat. No. 5,440,018.

[73] Assignee: The Green Cross Corporation, Osaka, Japan

[21] Appl. No.: 202,130

[22] Filed: Feb. 25, 1994

Related U.S. Application Data

[63] Continuation-in-part of Ser. No. 36,387, Mar. 24, 1993, Pat. No. 5,440,018.

[30] Foreign Application Priority Data

| May 20, 1992 | [JP] | Japan | 4-127673 |
| May 28, 1992 | [JP] | Japan | 4-137250 |
| Jul. 31, 1992 | [JP] | Japan | 4-205636 |
| Aug. 31, 1992 | [JP] | Japan | 4-232340 |
| Sep. 22, 1992 | [JP] | Japan | 4-253142 |
| Feb. 25, 1993 | [JP] | Japan | 5-037031 |
| Feb. 25, 1993 | [JP] | Japan | 5-037032 |

[51] Int. Cl.⁶ .......... C07K 14/765; C07K 1/16; C07K 1/36; A61K 38/38

[52] U.S. Cl. .......... 530/363; 530/364; 530/413; 530/414; 530/415; 530/416; 530/420

[58] Field of Search .......... 530/363, 364, 530/412, 414, 415, 416, 420, 413; 514/8, 21

[56] References Cited

U.S. PATENT DOCUMENTS 2,433,905  1/1948  Hughes .......... 530/364

(List continued on next page.)

FOREIGN PATENT DOCUMENTS 2001911  10/1989  Canada .......... 530/364

(List continued on next page.)

OTHER PUBLICATIONS

Kagaku Kogyo Wippo, Jul. 30, 1992.

(List continued on next page.)

Primary Examiner—Christina Y. Chan
Assistant Examiner—Nancy J. Degen
Attorney, Agent, or Firm—Sughrue, Mion, Zinn, Macpeak & Seas

[57] ABSTRACT

Human serum albumin obtained by gene manipulation techniques can be purified by a combination of specified steps in which a culture supernatant obtained from a human serum albumin-producing host is subjected to ultrafiltration, heat treatment, acid treatment and another ultrafiltration, followed by subsequent treatments with a cation exchanger, a hydrophobic chromatography carrier and an anion exchanger, and by salting-out to thereby obtain a pure form of human serum albumin which contains substantially no proteinous and polysaccharide contaminants, which is formulated into a pharmaceutical preparation. The thus obtained human serum albumin can further be purified by treating recombinant human serum albumin with a hydrophobic chromatography carrier at pH of 2 to 5 and a salt concentration of 0.4 to 1 and exposing the carrier to a pH of 6 to 8 and a salt concentration of 0.01 to 0.3 M, or treating the culture supernatant with boric acid or a salt thereof at pH 8 to 11 for 1 to 10 hours and recovering the supernatant. This process makes it possible to efficiently purify recombinant human serum albumin and to provide substantially pure human serum albumin which does not contain producer host-related substances and other contaminants and is sufficiently free from coloration.

10 Claims, 2 Drawing Sheets

U.S. PATENT DOCUMENTS

| | | | |
|---|---|---|---|
| 3,992,367 | 11/1976 | Plan et al. | 530/364 |
| 4,032,482 | 6/1977 | Moriya et al. | 521/29 |
| 4,289,690 | 9/1981 | Pestka et al. | 530/351 |
| 4,675,384 | 6/1987 | Dromard et al. | 530/364 |
| 4,677,027 | 6/1987 | Porath et al. | 428/407 |
| 4,990,447 | 2/1991 | König et al. | 435/71.1 |
| 5,250,663 | 10/1993 | Tenold | 530/364 |

FOREIGN PATENT DOCUMENTS

| | | | |
|---|---|---|---|
| 0319067 | 6/1989 | European Pat. Off. . | |
| 0420007 | 4/1991 | European Pat. Off. | 530/364 |
| 0428758 | 5/1991 | European Pat. Off. . | |
| 0464590 | 1/1992 | European Pat. Off. . | |
| 0570916 | 11/1993 | European Pat. Off. . | |

OTHER PUBLICATIONS

A. S. Michaels, "New Separation Technique for the CPI", *Chemical Engineering Progress* (vol. 64 No. 12) Dec. 1968, pp. 31–43.

E. L. V. Harris, *Protein Purification Methods*, 1989, pp. 151–157, 175–177, 232–235.

Candiano et al. "Determination of a glycosyl subunit of human serum albumin by concanavalin A–Sepherose" Clin Chim Acta 128:29–40 1983.

Andersson et al. "Purification of Commercial Human Albumin on Immobilized IDA–$Ni^{2+}$" J. Chromatog 421:141–146 1987.

Dandeu et al. "Isolation & Purification of Cat Albumin from Cat Serum by Copper Ion Affinity Chromatography: Further Analysis of Its Primary Structure" J Chromatog 539 475–484 1991.

FIG. 1A

CULTURE SUPERNATANT

ALBUMIN MONOMER

FIG. 1B

ELUATE FROM HYDROPHOBIC CHROMATOGRAPHY

ALBUMIN MONOMER

FIG. 2

RECOMBINANT HUMAN SERUM ALBUMIN, PROCESS FOR PRODUCING THE SAME AND PHARMACEUTICAL PREPARATION CONTAINING THE SAME

CROSS-REFERENCES TO RELATED APPLICATIONS

This is a continuation-in-part of application Ser. No. 08/036,387 filed on March 24, 1993 now U.S. Pat. No. 5,440,018.

FIELD OF THE INVENTION

The instant invention relates to a process for producing recombinant human serum albumin, in which the human serum albumin is purified through a combination of steps to yield a substantially pure form of human serum albumin.

BACKGROUND OF THE INVENTION

Albumin, especially human serum albumin (HSA), is an important protein of the circulatory system. The protein is produced in the liver and has a major role in maintaining normal osmotic pressure of body fluids, such as blood. It also serves as a carrier of various molecules.

HSA is administered under various clinical conditions. For example, in the case of shock or burn injury, it is necessary, in general, to administer HSA frequently to restore blood volume and to alleviate other injury-related symptoms. Patients suffering from hypoproteinemia and fetal erythroblastosis sometimes require HSA treatment.

In other words, a common indication for HSA administration is a loss of body fluids, such as during a surgical procedure, shock, burn injury or hypoproteinemia which causes edema.

Currently, HSA is produced mainly as a fractionated product of collected blood. Such a production process, however, has disadvantages in that it is not economical and the supply of blood is sporadic. In addition, collected blood sometimes contains undesirable substances, such as hepatitis virus. In consequence, it is profitable to develop a material which can be used as an HSA substitute.

Recent advances in recombinant DNA techniques have rendered possible microbial production of various types of useful polypeptides, and, as a result, a number of mammalian polypeptides already have been produced in various microorganisms. With regard to HSA, establishing techniques for the large scale production of HSA by recombinant methods and subsequent high grade purification also is in progress.

Techniques for the isolation and purification of HSA from plasma have been studied from various points of view and put into practical use. For example, the ethanol fractionation method of E. J. Cohn et al., PEG fractionation method, ammonium sulfate fractionation method and the like are well known methods. In addition to those methods, several purification processes recently have been developed, such as, for example, a process in which an anion exchanger treatment and a heat treatment at 60° C. for 10 hours are employed in combination (JP-A-2-191226 corresponding to EP-A-367220) and a process in which an anion exchanger treatment, a cation exchanger treatment and a heat treatment at 60° C. for 10 hours are employed in combination (JP-A-3-17123 corresponding to EP-A-428758). (The term "JP-A" as used herein means an "unexamined published Japanese patent application".)

However, in the case of producing HSA by means of gene manipulation techniques, it is highly probable that an HSA preparation of interest will be contaminated by certain coloring components which are contained in the raw materials or secreted by a microorganism during culturing of the host microorganism or are introduced during purification of the resulting HSA, and that those contaminants bind to HSA to cause coloring of the HSA itself. What is more, such contaminants cannot be removed sufficiently by means of any prior art process for the purification of plasma-derived HSA.

SUMMARY OF THE INVENTION

Taking the aforementioned problems involved in the prior art into consideration, the instant inventors have conducted intensive studies and, as a result, succeeded in developing a process for efficiently purifying HSA obtained by gene manipulation techniques.

An object of the instant invention is to provide human serum albumin obtained by means of gene manipulation techniques, which does not contain producer host-related substances or other contaminants and is substantially free from coloring.

More specifically, the instant invention provides a process for producing a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of 3 to 5 to yield an acid-treated sample;

(4) treating the acid-treated sample using an ultrafiltration membrane having a molecular weight exclusive limit of from 100,000 to 500,000 to yield a second filtrate;

(5) allowing the second filtrate to contact with a cation exchanger at a pH of 3 to 5 and a salt concentration of 0.01 to 0.2M, and then exposing the cation exchanger to a pH of 8 to 10 and a salt concentration of 0.2 to 0.5M to yield a first eluate;

(6) allowing the first eluate to contact with a carrier for hydrophobic chromatography at a pH of 6 to 8 and a salt concentration of 0.01 to 0.5M, and recovering non-adsorbed fractions to yield a second eluate; and (7) allowing the second eluate to contact with an anion exchanger at a pH of 6 to 8 and recovering non-adsorbed fractions to yield the albumin.

An additional step (8) may be employed in the above process, in which the resulting eluate of step (7) further is allowed to contact with a chelate resin and the resulting nonadsorbed fractions are recovered.

Another object of the instant invention is to provide a process for producing a recombinant human serum albumin which substantially contain no free nonantigenic contaminants detectable by the phenol-sulfuric acid method, which comprises the steps of allowing the recombinant human serum albumin to contact with a carrier for hydrophobic chromatography at a pH of 2 to 5 and a salt concentration of 0.4 to 1M and exposing the carrier to a pH of 6 to 8 and a salt concentration of 0.01 to 0.3M, or treating the recombinant human serum albumin with boric acid or a salt thereof to remove contaminants, which may be followed by treatment with a ultrafiltration membrane having a molecular weight exclusive limit of about 100,000.

Another object of the instant invention is to provide a substantially pure recombinant human serum albumin, wherein a 25% solution of the albumin contains contaminated proteins in an amount of 0.1 ng/ml or less and contaminated polysaccharides in an amount of 1 ng/ml or less.

Another object of the instant invention is to provide a recombinant human serum albumin, wherein a content of free nonantigenic contaminants detectable by the phenol-sulfuric acid method is 1 µg or less per 250 mg of said albumin, a content of producer host-related antigenic contaminants is 0.1 ng or less and a content of pyrogen is 0.1 EU or less.

Still another object of the instant invention is to provide a pharmaceutical preparation comprising recombinant human serum albumin, acetyltryptophan or a salt thereof and sodium caprylate.

DETAILED DESCRIPTION OF THE INVENTION

The term "substantially pure HSA" used herein means that a 25 w/v% aqueous solution of purified HSA contains contaminated proteins and polysaccharides in an amount of at most 0.1 ng/ml or below and 1 ng/ml or below, respectively, or that the purity of purified HSA is 99.999999% or more.

In the process of the instant invention, the step (6) may be replaced by another step (6) in which the resulting eluate of the step (5) is allowed to contact with a carrier for hydrophobic chromatography at a pH of 6 to 8 and a salt concentration of 1 to 3M, and then the carrier is exposed to a pH of 6 to 8 and a salt concentration of 0.01 to 0.5M.

Also, the step (7) of the process of the present invention may be replaced by another step (7) in which the resulting eluate of the step (6) is allowed to contact with an anion exchanger at a pH of 6 to 8 and a salt concentration of 0.001 to 0.05M, and then the anion exchanger is exposed to a pH of 6 to 8 and a salt concentration of 0.05 to 1M.

In addition, the process of the present invention may further comprise a salt precipitation (salting-out) step following step (5), step (6) or step (7), in which the salt precipitation is carried out by exposing the first eluate, the second eluate or the albumin to a pH of 3 to 5 and a salt concentration of 0.5 to 3M to yield a precipitation and dissolving the precipitate in a buffer.

The instant invention is described in detail below.

(1) Recombinant HSA

The HSA-producing host prepared by means of gene manipulation techniques to be used in the instant invention is not limited so long as the HSA has been prepared via gene manipulation techniques, hence the host can be selected from hosts already known in the art, as well as those hosts which will be developed in the future. Illustrative examples of the host include microbial cells, such as *Escherichia coli*, various yeast species, *Bacillus subtilis* and the like, and animal cells. Particularly preferred hosts are yeast species, especially those belonging to the genus Saccharomyces, such as *Saccharomyces cerevisiae*, or the genus Pichia, such as *Pichia pastoris*. Auxotrophic strains or antibiotic-sensitive strains also may be used. *Saccharomyces cerevisiae* AH22 (a, his 4, leu 2, can 1), *Pichia pastoris* GTS115 (his 4) and the like strains are used preferably.

Preparation of the HSA-producing hosts, production of HSA by culturing the hosts and isolation and recovery of HSA from the resulting culture broth may be effected using known techniques or modified procedures thereof. For example, preparation of an HSA-producing host (or an HSA-producing strain) may be effected using a process in which a natural human serum albumin gene is used (JP-A-58-56684 corresponding to EP-A-73646, JP-A-58-90515 corresponding to EP-A-79739 and JP-A-58-150517 corresponding to EP-A-91527), a process in which a modified human serum albumin gene is used (JP-A-62-29985 and JP-A-1-98486 corresponding to EP-A-206733), a process in which a synthetic signal sequence is used (JP-A-1-240191 corresponding to EP-A-329127), a process in which a serum albumin signal sequence is used (JP-A-2-167095 corresponding to EP-A-319641), a process in which a recombinant plasmid is introduced into chromosome (JP-A-3-72889 corresponding to EP-A-399455), a process in which hosts are fused (JP-A-3-53877 corresponding to EP-A-409156), a process in which mutation is generated in a methanol containing medium, a process in which a mutant AOX2 promoter is used (EP-A-506040), a process in which HSA is expressed in *B. subtilis* (JP-A-62-215393 corresponding to EP-A-229712), a process in which HSA is expressed in yeast (JP-A-60-41487 corresponding to EP-A-123544, JP-A-63-39576 corresponding to EP-A-248657 and JP-A-63-74493 corresponding to EP-A-251744) and a process in which HSA is expressed in Pichia (JP-A-2-104290 corresponding to EP-A-344459).

The process in which mutation is generated in a methanol-containing medium is carried out in the following manner.

Firstly, a plasmid containing a transcription unit which is constructed so as to express HSA under the control of AOX1 promoter is introduced into the AOX1 gene region of an appropriate host, preferably a Pichia yeast, more preferably Pichia strain GTS115 (NRRL deposition number Y-15851) (JP-A-2-104290 corresponding to EP-A-344459) to obtain a transformant. Since the thus obtained transformant does not grow well in a methanol-containing medium, mutation of the transformant is effected by culturing the transformant in a methanol-containing medium to isolate a mutant strain which is capable of growing in the medium. The methanol concentration in the medium may be in the range of approximately from 0.01 to 5%. The medium may be either synthetic or natural, and the culturing may be carried out at 15° to 40° C. for 1 to 1,000 hours.

Culturing of an HSA-producing host (an HSA production process) may be carried out using known processes disclosed in the aforementioned references, or in accordance with a process disclosed in JP-A-3-83595 in which high concentration substrate inhibition of HSA producer cells is avoided by gradually adding a high concentration glucose solution to a medium by means of fed batch fermentation, thereby enabling production of both the producer cells and the product in high concentrations, or in accordance with another process disclosed in JP-A-4-293495 corresponding to EP-A-504823 in which productivity of HSA is improved by adding fatty acids to a medium.

Isolation and recovery of HSA may be carried out using known processes disclosed in the aforementioned references, or in accordance with a process disclosed in JP-A-3-103188 corresponding to EP-A-420007 in which proteases are inactivated by heat treatment or a coloration inhibition process disclosed in JP-A-4-54198 corresponding to U.S. Pat. No. 5,132,404 or EP-A-464590 in which HSA is separated from coloring substances using at least one adsorbent selected from the group consisting of anion exchangers, hydrophobic carriers and activated charcoal.

The medium for culturing a transformed host may be prepared by adding fatty acids having 10 to 26 carbon atoms, or salts thereof, to a known medium, and culturing the transformant under known conditions. The medium may be either synthetic or natural, but preferably a liquid medium. For example, a suitable synthetic medium may be composed of: carbon sources, such as various saccharide and the like; nitrogen sources, such as urea, ammonium salts, nitrates and the like; trace nutrients, such as various vitamins, nucleotides and the like; and inorganic salts, such as of Mg, Ca, Fe, Na, K, Mn, Co, Cu and the like. An illustrative example of such a medium is YNB liquid medium which consists of 0.7% Yeast Nitrogen Base (Difco) and 2% glucose. An illustrative example of a useful natural medium is YPD liquid medium which consists of 1% Yeast Extract (Difco), 2% Bacto Peptone (Difco) and 2% glucose. The medium pH may be neutral, weakly basic or weakly acidic. In the case of a methanol assimilating host, the medium may be further supplemented with methanol in an amount of approximately from 0.01 to 5%.

Culturing of a host may be carried out preferably at 15° to 43° C. (20° to 30° C. for yeast strains, 20 to 37° C. for bacterial strains) for 1 to 1,000 hours, by means of static or shaking culturing or batch, semi-batch or continuous culturing under agitation and aeration.

In that instance, it is desirable to prepare a seed culture prior to the batch culturing. The seed culturing may be carried out using the aforementioned YNB liquid medium or YPD liquid medium, preferably at 30° C. (yeast) or 37° C. (bacterium) and for 10 to 100 hours.

After completion of the culturing, HSA is recovered from the resulting culture medium or cells in the usual way.

(2) Purification of HSA (i) Ultrafiltration

High molecular weight substances other than HSA, as well as low molecular weight substances, are separated and removed from a culture supernatant obtained after separation of HSA-producing host cells, using ultrafiltration techniques.

High molecular weight substances are removed using an ultrafiltration membrane having a molecular weight exclusive limit of approximately from 100,000 to 500,000, preferably around 300,000, and low molecular weight substances are removed using another ultrafiltration membrane having a molecular weight exclusive limit of approximately from 1,000 to 50,000, preferably from about 10,000 to about 30,000.

Separation of remaining HSA-producing host cells is effected simultaneously at the time of the removal of high molecular weight substances, and concentration of the liquid is effected at the time of the removal of low molecular weight substances.

(ii) Heat treatment

The concentrated solution obtained in the above step (i) is subjected to heat treatment at 50° to 70° C. for approximately 30 minutes to 5 hours, preferably at 60° C. for approximately 1 to 3 hours.

Preferably, the heating is conducted in the presence of a stabilizing agent. Preferred examples of the stabilizer include acetyltryptophan and an organic carboxylic acid having 6 to 18 carbon atoms, or a salt thereof. The stabilizers may be used in combination. Acetyltryptophan may be used in an amount of approximately from 1 to 100 mM. Illustrative examples of the organic carboxylic acid having 6 to 18 carbon atoms include caproic acid (6 carbon atoms), caprylic acid (8 carbon atoms), capric acid (10 carbon atoms), lauric acid (12 carbon atoms), palmitic acid (16 carbon atoms), oleic acid (18 carbon atoms) and the like. Illustrative examples of the salts include alkali metal salts such as sodium salt, potassium salt and the like, and alkaline earth metal salts, such as calcium salt and the like. The organic carboxylic acid having 6 to 18 carbon atoms or a salt thereof may be used in an amount of approximately from 1 to 100 mM.

In the heat treatment step, color development caused by the heating can be prevented by the addition of a thiol compound (for example, mercaptoethanol, cysteine, reduced glutathione or the like) in an amount of approximately from 1 to 100 mM, preferably from 5 to 30 mM, and aminoguanidine in an amount of from 10 to 1,000 mM. A part of this step has already been disclosed in JP-A-3-103188.

(iii) Acid treatment

The heat-treated solution of the above step (ii) is adjusted to a pH of approximately 3 to 5, preferably 4 to 4.6, with acid and then allowed to stand for a period of approximately 1 to 12 hours. Examples of the acid include acetic acid, hydrochloric acid, phophoric acid, sulfuric acid and the like.

(iv) Ultrafiltration

In this step, polymerized high molecular weight contaminants are removed by ultrafiltration. High molecular weight substances are removed using an ultrafiltration membrane having a molecular weight exclusive limit of approximately from 100,000 to 500,000, preferably around 300,000. If necessary, buffer exchange may be carried out for use in the following cation exchanger treatment, using an ultrafiltration membrane having a molecular weight exclusive limit of approximately from 1,000 to 50,000, preferably from about 10,000 to about 30,000.

(v) Cation exchanger treatment

Usable as cation exchangers are those having sulfo groups, carboxyl groups and the like. Illustrative examples of the sulfo group-containing cation exchangers include sulfoagarose (trade name, S-Sepharose®, available from Pharmacia), sulfopropyl-dextran (trade name, SP-Sephadex®, available from Pharmacia), sulfopropyl-polyvinyl (trade name, SP-Toyopearl®, available from Tosoh Corp.) and the like. Illustrative examples of the carboxyl group-containing cation exchangers include carboxymethyl-dextran (trade name, CM-Sephadex®, available from Pharmacia; and trade name, CM-Cellulofine®, available from Seikagaku Corp.) and the like.

The exchanger can be equilibrated with an appropriate buffer such as acetate buffer having a pH of approximately 3 to 5, preferably 4 to 4.6 and containing a salt such as sodium chloride in a concentration of approximately 0.01 to 0.2M, preferably 0.05 to 0.1M. The same buffer can be used for contacting and washing treatments. Elution may be effected with an appropriate buffer such as phosphate buffer having a pH of generally 8 to 10, preferably 8.5 to 9.5 and containing a salt such as sodium chloride in a concentration of generally 0.2 to 0.5M, preferably 0.3 to 0.4M.

(vi) First hydrophobic chromatography

Carriers for use in hydrophobic chromatography include those containing an alkyl group (butyl group, octyl group, octyldecyl group and the like), each group having 4 to 18 carbon atoms, and those containing a phenyl group. Illustrative examples of the butyl group-containing carriers include butyl-agarose, butyl-polyvinyl (trade name, Butyl Toyopearl®, available from Tosoh Corp.) and the like, those of the octyl group-containing and octyldecyl group-containing carriers include octyl-agarose and octyldecyl-agarose, respectively, and those of the phenyl group-containing carrier include phenyl-cellulose (trade name, Phenyl Cellulofine®, available from Seikagaku Corp.) and the like.

In this step, HSA can be recovered from non-adsorbed fractions. In that case, contacting may be effected using an appropriate buffer such as phosphate buffer having a pH of approximately 6 to 8, preferably 6.5 to 7 and containing a salt such as sodium chloride in a concentration of approximately 0.01 to 0.5M, preferably 0.05 to 0.2M.

HSA also can be recovered by elution after adsorption to the aforementioned carrier. In that case, contacting and washing may be carried out using an appropriate buffer such as phosphate buffer having a pH of approximately 6 to 8, preferably from 6.5 to 7 and containing a salt such as sodium chloride in a concentration of approximately 1 to 3M, preferably 1.5 to 2M. The elution may be effected with an appropriate buffer such as phosphate buffer having a pH of approximately 6 to 8, preferably 6.5 to 7 and containing a salt such as sodium chloride in a concentration of approximately 0.01 to 0.5M, preferably 0.05 to 0.2M.

(vii) Anion exchanger treatment

Examples of anion exchangers include those containing the diethylaminoethyl (DEAE) group, those containing a quaternary aminoethyl (QAE) group and the like. Illustrative examples of the DEAE group-containing anion exchangers include DEAE-agarose (trade name, DEAE-Sepharose®, available from Pharmacia), DEAE-dextran (trade name, DEAE-Sephadex®, available from Pharmacia), DEAE-polyvinyl (trade name, DEAE-Toyopearl®, available from Tosoh Corp.) and the like. Illustrative examples of the QAE group-containing anion exchangers include QAE-agarose (trade name, Q-Sepharose®, available from Pharmacia), QAE-polyvinyl (trade name, QAE-Toyopearl®, available from Tosoh Corp.) and the like.

In this step, HSA can be recovered from non-adsorbed fractions. In that case, contacting may be effected using an appropriate buffer such as phosphate buffer having a pH of approximately 6 to 8, preferably 6.5 to 7 and a salt concentration of approximately 0.01 to 0.1M.

HSA also can be recovered by elution after adsorption to the aforementioned carrier. In that case, contacting and washing may be carried out using the same buffer as described above except for containing a salt such as sodium chloride in a concentration of 0.001 to 0.05M and elution may be carried out with the same buffer but having a salt concentration of 0.05 to 1M.

(viii) Salting-out

In this step, HSA is precipitated specifically by adding a salt component to the sample solution to a final salt concentration of approximately 0.1 to 3M, preferably 0.5 to 1.5M and then adjusting the resulting solution to a pH of approximately 3 to 5, preferably 3.5 to 4.5. Impurities in the supernatant fluid are removed by separating the HSA precipitate.

The thus precipitated HSA is dissolved in an appropriate buffer solution. Though not particularly limited, usable as salt components to adjust ionic strength are sodium chloride, potassium chloride, ammonium sulfate, sodium (or potassium) thiocyanate, sodium sulfate and the like. Also, though not particularly limited, separation of the precipitated HSA from the supernatant fluid may be effected preferably by centrifugation, press separation, cross-flow membrane separation and the like.

This step may be carried out preferably after the anion exchanger treatment step (vii), but may also be interposed between the cation exchanger treatment step (v) and the hydrophobic chromatography treatment step (vi) or between the hydrophobic chromatography treatment step (vi) and the anion exchanger treatment step (vii).

(ix) Chelate resin treatment

The above purification steps may further contain a step of allowing HSA to contact with a chelate resin which has a specified ligand moiety. This step may be carried out preferably after the anion exchanger treatment or salting-out precipitation treatment, whichever is the later.

Preferably, the carrier moiety of the chelate resin may have hydrophobic nature. Examples of such a type of carrier moiety include a copolymer of styrene and divinylbenzene, a copolymer of acrylic acid and methacrylic acid and the like.

Examples of the ligand moiety include a thiourea group, as well as a polyamine group (including a polyalkylene polyamine group such as polyethylene polyamine or the like) which contains, in one molecule, a plurality of subgroups consisting of a polyol group such as an N-methylglucamine group, an imino group, an amino group, an ethyleneimino group and the like. Illustrative examples of preferred commercially available chelate resins having the above-described carrier and ligand moieties, include DIAION CRB02® (ligand moiety, N-methylglucamine group, available from Mitsubishi Kasei Corp.), DIAION CR20® (ligand moiety, $-NH(CH_2CH_2NH)_nH$, available from Mitsubishi Kasei Corp.), LEWATIT TP214® (ligand moiety, $-NHCSNH_2$, available from bayer) and AMBERLITE CG4000®, all of which have a copolymer of styrene and divinylbenzene as the carrier moiety.

Preferred conditions for the chelate resin treatment are as follows:

pH: acidic or neutral (pH 3 to 9, preferably 4 to 7), period: at least 1 hour, preferably 6 hours or more, ionic strength: 50 mmho or less, preferably 1 to 10 mmho, mixing ratio: 0.1 to 100 g, preferably 1 to 10 g, of the resin based on 250 mg of HSA (wet basis).

In the process, contaminated coloring substances derived from the raw material or the host are adsorbed to the chelate resin, thus enabling reduction of coloration of HSA.

The steps (v), (vi), (vii) and (ix) may be carried out using a column or in a batchwise operation, with the use of a column being preferred.

Salting-out step (viii) can also be carried out after chelate resin treatment step (ix) and prior to the below-described second hydrophobic chromatography step (x).

(x) Second hydrophobic chromatography

Free nonantigenic contaminants detectable by the phenol-sulfuric acid method are not fully removed from the HSA obtained through the above-described steps (i) to (vii) and (ix).

The HSA obtained through the above-described treatments is allowed to contact with a carrier for hydrophobic chromatography at a pH of 2 to 5, preferably 3 to 4 and a salt concentration of 0.4 to 1M, preferably 0.4 to 0.7M. The elution can be effected at a pH of 6 to 8, preferably 6.5 to 7 and a salt concentration of 0,01 to 0.3M, preferably 0.05 to 0.2M. The above-described step (vi) may be replaced with this hydrophobic chromatography step. Thus, HSA which does not contain free nonantigenic contaminants detectable by the phenol-sulfuric acid method can be recovered.

The term "phenol-sulfuric acid treatment" used herein means one of colorimetric determination of carbohydrates which comprises adding a phenol solution to a sample carbohydrate solution, adding concentrated sulfuric acid thereto, shaking the mixture to allow a furfural derivative derived from the carbohydrate utilizing heat of solution to react with phenol and colorimetrically determining the resulting colored reaction product. The free nonantigenic contaminants detectable by the phenol-sulfuric acid method include neutral carbohydrates such as pentose and hexose, monocarbohydrate glycoside such as oligosaccharides, complex carbohydrates and uronic acid, methylated carbohydrate and the like. These contaminants do not cause antigert-antibody reaction with antibodies against producer host-derived substances.

Carriers for use in the second hydrophobic chromatography are the same as those used in the first hydrophobic chromatography.

HSA which does not contain free nonantigenic contaminants detectable by the phenol-sulfuric acid method can be obtained by a treatment with a ConA-immobilized carrier such as ConA-Sepharose (Pharmacia) and the like in place of this hydrophobic chromatography treatment. The ConA treatment can be carried out by contacting the HSA fraction with a ConA-immobilized carrier either in a batchwise or column operation at a pH of 6 to 8 and a salt concentration of 0.01 to 0.1M and recovering non-adsorbed fractions.

(xi) Treatment with boric acid or a salt thereof.

Instead of the above treatment (x), the HSA obtained through the above-described steps (i) to (vii) and (ix) can be treated with boric acid or a salt thereof to remove antigenic producer host-derived contaminants and pyrogen as well as free nonantigenic contaminants detectable by the phenol-sulfuric acid method.

Examples of the boric acid include orthoboric acid, metabolic acid, tetraboric acid and the like. The salts thereof include alkali metal salts such as sodium salt and potassium salt, alkaline earth metal salts such as calcium salt, and the like. Calcium tetraborate is preferably used. Boric acid or a salt thereof is added to a final concentration of about 0.01 to 1M, preferably about 0.05 to 0.2 treatment can be carried out at a pH of about 8 to 11, preferably about 9 to 10 for about 1 to 10 hours. This treatment is preferably effected at a low electric conductivity, for example, 1 mS or less. The HSA concentration is preferably low, for example, 5% or less, more preferably about 0.1 to 3%.

After the treatment with boric acid or a salt thereof, the precipitate formed is removed by, for example, centrifugation or filtration and the supernatant is recovered, concentrated and desalted.

(xii) Ultrafiltration

The HSA obtained after the above step (xi) is preferably subjected to ultrafiltration using an ultrafiltration membrane having a molecular weight exclusive limit of about 100,000.

HSA thus purified through the above steps is substantially free from coloring, which means a coloring degree of the purified HSA ranges approximately from 0.001 to 0.005 in terms of an $A_{500\ nm}/A_{280\ nm}$ ratio in a 25% HSA solution. The term "a 25% HSA solution" used herein means a solution of 25% protein which may contain contaminated proteins in an amount lower than the detection limit, namely 0.1 ng/ml, other than purified HSA. Coloration of HSA is reduced to a level of from ½ to ⅒ by the chelate resin treatment of the instant invention. Especially, absorbance at around 500 nm, namely reddish coloration, is reduced to a level of from ⅓ to ⅒.

In addition, fatty acids which adsorb or bind to HSA, derived from the medium or the host or secreted by the host, can be removed by the chelate resin treatment.

Amounts of fatty acids adsorbed to HSA which has been purified through the above steps (i) to (vii) and the additional salting-out step are reduced to a level of ⅒ or below, preferably ¹⁄₁₀₀ or below, by the chelate resin treatment.

Amounts of fatty acids adsorbed to HSA can be measured in accordance with a generally used means such as Duncombe's extraction method (Clin. Chim. Acta., 9, 122–125 (1964)) or acyl-CoA synthetase (ACS)-acyl-CoA oxidase (ACOD) method in which ACS and ACOD are used.

The Duncombe's extraction method comprises, in principle, converting fatty acids into copper salts using a copper reagent, extracting with chloroform and then subjecting the extract to color development with Bathocuproin. The method can be carried out easily using a kit such as NEFA-Test Wako® (Wako Pure Chemical Industries, Ltd.) which contains Bathocuproin.

On the other hand, the ACS-ACOD method comprises, in principle, reacting fatty acids with acyl-CoA synthetase and acyl-CoA oxidase to generate $H_2O_2$ and exposing the thus formed $H_2O_2$ by a color development scheme using oxidation-condensation reaction of a chromogenic substance in the presence of peroxidase. That method also can be carried out easily using a measuring kit such as NEFAC-Test Wako® (Wako Pure Chemical Industries, Ltd.).

Substances to be removed by the defatting method of the present invention are fatty acids and esters thereof which are derived from raw materials for HSA production, such as that derived from blood, a medium, a host or those secreted by the host.

Examples of fatty acids to be removed include saturated fatty acids having 8 to 20 carbon atoms, such as palmitic acid, stearic acid and the like, and unsaturated fatty acids having 16 to 20 carbon atoms, such as oleic acid, linoleic acid, arachidonic acid and the like.

Since this step is effective for the removal of those fatty acids, it can be applied to the defatting of HSA molecules to which those fatty acids are attached, independent of the origin of the HSA.

(3) Pharmaceutical preparation

The HSA thus obtained may be made into pharmaceutical preparations by generally known means such as 10 hours of heat sterilization at 60° C., ultrafiltration, filter sterilization, dispensation, freeze-drying and the like. An illustrative example of the pharmaceutical preparation of the present invention is a liquid preparation which contains HSA in an amount of 5 to 25%, has a pH of approximately 6.4 to 7.4 and has an osmotic pressure ratio of around 1.

The HSA-containing pharmaceutical preparation of the instant invention may contain stabilizers which include acetyltryptophan or a salt thereof (e.g., sodium salt) and sodium caprylate. Each stabilizer may be used in an amount of approximately 0.001 to 0.2M, preferably 0.01 to 0.05M in a 25% HSA solution. The sodium content may be 3.7 mg/ml or less. The HSA preparation may further contain pharmaceutically acceptable additives such as sodium chloride and the like.

In general, the stabilizers may be added prior to the aforementioned preparation steps such as 10 hours of heat sterilization at 60° C., ultrafiltration, filter sterilization, dispensation, freeze-drying and the like. Therefore, not only preservation stability of HSA but also its stability during the preparation process of the pharmaceutical preparation of the instant invention can be improved.

The HSA-containing pharmaceutical preparation thus obtained can be used clinically as injections in the same manner as the case of the prior art plasma-derived HSA preparations. For example, it may be used for the purpose of rapidly increasing blood volume, mainly at the time of shock, supplementing circulation blood volume, improving hypoproteinemia or maintaining collagen osmotic pressure. More illustratively, the HSA-containing pharmaceutical preparation of the present invention can be used effectively for the treatment of hypoalbuminemia caused by the loss of albumin (burn injury, nephrotic syndrome or the like) or by the reduction of albumin synthesizing ability (hepatic cirrhosis or the like), as well as for the treatment of hemorrhagic shock and the like.

The pharmaceutical preparation may be administered gradually by intravenous injection or intravenous drip infusion, with a dose of generally from 20 to 50 ml as a 25% HSA solution (5 to 12.5 g as HSA) per one administration for an adult. The dose may be changed optionally depending on the age, symptoms, weight and the like of the patient. Properties of the purified recombinant HSA.

(4) Purified HSA

The HSA of the instant invention is a homogeneous substance having a molecular weight of about 67,000 and an isoelectric point of 4.6 to 5.0. The HSA consists of a monomer and contains substantially no dimers, polymers or decomposed products. In fact, the total content of dimers, polymers and hydrolyzed products is approximately 0.01% or less.

Also, the HSA of the instant invention contains substantially no producer host-derived contaminants, such as protein, polysaccharide and the like, which means contaminants having antigenecity detectable by immunoassay such as EIA, RIA, PHA and so forth. Thus, the HSA of the instant invention contains substantially no host-derived contaminants having antigenecity detectable by immunoassay. In the case of a 25% HSA solution, the protein content may be 1 ng/ml or below, preferably 0.1 ng/ml or below, and the polysaccharide content may be 10 ng/ml or below, preferably 1 ng/ml or below. In that case, the purity of the HSA is calculated to be 99.999999% or more, preferably 99.9999999% or more.

The degree of coloring of the 25% HSA solution may be in the range of from 0.01 to 0.05 in terms of an $A_{350}/A_{280}$ ratio, from 0.001 to 0.02 as an $A_{450}/A_{280}$ ratio and from 0.001 to 0.005 as an $A_{500}/A_{280}$ ratio.

Further, the amount of fatty acids linked to the HSA may be one molecule or less, preferably 0.1 molecule or less, per one HSA molecule.

Furthermore, the content of free nonantigenic contaminants detectable by the phenol-sulfuric acid method is 1 μg or less, that of antigenic producer host-related contaminants is 0.1 ng or less and that of pyrogen is 0.1 EU or less.

According to the instant invention, recombinant HSA can be purified efficiently. In addition, the instant invention can provide substantially pure recombinant HSA which does not contain producer host-related substances and other contaminants, and is sufficiently free from coloration.

The following examples are provided to further illustrate the instant invention. It is to be understood, however, that the examples are not to limit the scope of the present invention.

REFERENCE EXAMPLE 1

(1) Used strain, *Pichia pastoris* GCP101

A strain of *Pichia pastoris*, PC4130, obtained in accordance with the process disclosed in JP-A-2-104290, was made by digesting a plasmid pPGP1, containing a transcription unit which is constructed so as to express HSA under the control of an AOX1 promoter, with NotI and then substituting the resulting NotI-digested fragment for the AOX1 gene region of a *Pichia pastoris* strain GTS115 (his4). The strain does not grow well in a medium containing methanol as the carbon source (Mut⁻ strain) because of the deletion of the AOX1 gene.

The strain PC4130 was inoculated into 3 ml of YPD medium (1% yeast extract, 2% Bacto Peptone and 2% glucose). After 24 hours of culturing, the cells were inoculated into 50 ml of YPD medium so that the cell density should be adjusted to initial turbidity with an $OD_{540}$ of 0.1. After 3 days of culturing at 30° C., the resulting cells again were inoculated into 50 ml of YPD medium at an initial cell turbidity of 0.1 at OD540. Thereafter, subculturing was repeated every 3 days in the same manner. After each subculturing, cells were diluted with sterile water and poured onto a 2% MeOH-YNBw/oa.a. plate (0.7% Yeast Nitrogen Base without Amino Acids, 2% methanol and 1.5% agar powder) in an inoculum size of $10^7$ cells/plate, followed by 5 days of culturing at 30° C. to judge the present/absence of colonies. Twenty colonies were found on the 2% MeOH-YNBw/oa.a. plate after 12 days of the successive subculturing. Mut⁻ strains can hardly grow on the 2% MeOH-YNBw/oa.a. medium while Mut⁺ strains can grow well. That is, advent of a colony means that the strain acquired the capacity of increased methanol assimilation and thus a Mut⁺ strain was obtained. One of the thus obtained colonies was diluted appropriately with sterile water and spread onto a 2% MeOH-YNBw/oa.a. plate to isolate single colonies. One of the resulting single colonies was named GCP101.

(2) Culturing of the strain (First seed culture)

A 1 ml portion of the strain which had been frozen in glycerol was inoculated into a 1,000 ml baffled Erlenmeyer flask containing 200 ml of YPD medium (see Table 1) and cultured at 30° C. for 24 hours with shaking.

TABLE 1

| Composition of YPD medium | |
| --- | --- |
| Components | Concentration (g/L) |
| Yeast extract | 10 |
| Peptone | 20 |
| Glucose | 20 |

(Second seed culture)

The first seed culture broth was inoculated into a 10 liter-jar fermentor containing 5 liters of YPD medium, and the second seed culturing was carried out at 30° C. for 24 hours with agitation and at an aeration rate of 5 liters per minutes. In the seed culturing, the pH of the medium was not controlled.

(Main culture)

The second seed culture broth was transferred into a 1,200 liter-fermentor containing 250 liters of a batch culture medium (see Table 2), and batch culturing was started with agitation and aeration under an internal pressure of 0.5 kg/cm² and at a maximum aeration rate of 800 liter/min under atmospheric pressure. The agitation rate was controlled so that the level of dissolved oxygen in the medium was maintained at approximately 50 to 30% of the saturated dissolved oxygen concentration. When the glycerol in the batch culture medium was consumed, addition of a feeding medium (see Table 3) was started. Feeding rate of the medium was controlled using a computer in such a manner that methanol did not accumulate in the culture medium, thereby effecting a high density culturing. The medium pH was controlled at a fixed level of 5.85 by the addition of 28% aqueous ammonia. For defoamation of the culture medium, an antifoam agent (Adecanol®, manufactured by Asahi Denka Kogyo K.K.) was added in an amount of 0.30 ml/liter at the time of the commencement of the batch culture, thereafter adding a small amount when required.

TABLE 2

Composition of batch culture medium

| Components | Amount per liter |
| --- | --- |
| Glycerol | 50.0 g |
| $H_3PO_4$ (85%) | 14.0 ml |
| $CaSO_4.2H_2O$ | 0.6 g |
| $K_2SO_4$ | 9.5 g |
| $MgSO_4.7H_2O$ | 7.8 g |
| KOH | 2.6 g |
| Biotin solution *1 | 1.6 ml |
| YTM solution *2 | 4.4 ml |
| *1 Biotin solution: 0.2 g/l | |
| *2 YTM solution: | |
| $FeSO_4.7H_2O$ | 65.0 g |
| $CuSO_4.5H_2O$ | 6.0 g |
| $ZnSO_4.7H_2O$ | 20.0 g |
| $MnSO_4.4–5H_2O$ | 3.0 g |
| $H_2SO_4$ | 5.0 ml |

TABLE 3

Composition of feeding medium

| Components | Amount |
| --- | --- |
| YTM solution | 2 ml |
| Methanol | 1,000 ml |

REFERENCE EXAMPLE 2

An HSA expression plasmid pMM042 was constructed using an AOX2 promoter (a mutant of the natural AOX2 promoter (*YEAST*, 5, 167–177, 1988; *Mol. Cell. Biol.*, 9, 1316–1323, 1989), in which the 255th base upstream from the initiation codon of said promoter is changed from T to C) isolated from the strain GCP101 obtained in Reference Example 1. The thus constructed plasmid was introduced into *Pichia pastoris* GTS115 to obtain a transformant UHG42-3 (EP-A-506040). Thereafter, the thus obtained transformant was cultured in accordance with the procedure of Reference Example 1, thereby allowing the transformant to produce HSA.

EXAMPLE 1

[i] Isolation of culture supernatant-membrane fractions (I) and (II)

About an 800 liter portion of the culture broth obtained in Reference Example 1 was subjected to a filter press to isolate the culture supernatant. The resulting supernatant subsequently was treated with an ultrafiltration membrane having a molecular weight exclusive limit of 300,000. Then, the resulting filtrate was concentrated to a volume of about 80 liters using an ultrafiltration membrane having a molecular weight exclusive limit of 30,000 [membrane fraction (I)].

Next, the membrane fraction (I) was heat-treated at 60° C. for 3 hours in the presence of 5 mM of sodium caprylate, 10 mM of cysteine and 100 mM of aminoguanidine at pH 7.5. The thus heat-treated solution was cooled down rapidly to about 15° C., adjusted to pH 4.5 and then treated with an ultrafiltration membrane having a molecular weight exclusive limit of 300,000 [membrane fraction (II)]. Thereafter, using an ultrafiltration membrane having a molecular weight exclusive limit of 30,000, the buffer in the resulting albumin solution was replaced by a 50 mM acetate buffer (pH 4.5) containing 50 mM of sodium chloride.

[ii] Cation exchanger treatment

The albumin solution obtained in the above step [i] was applied to a column packed with S-Sepharose® which had been equilibrated in advance with a 50 mM acetate buffer (pH 4.5) containing 50 mM of sodium chloride, the column was washed thoroughly with the same buffer and then elution was carried out with a 0.1M phosphate buffer (pH 9) containing 0.3M sodium chloride.

Polysaccharide content before and after the cation exchanger treatment was measured in accordance with the phenol-sulfuric acid method to find that the polysaccharide content has been reduced by 1/20 by this treatment.

[iii] Hydrophobic chromatography

The albumin solution eluted from the S-Sepharose® column was applied to a column packed with Phenyl Cellulofine® which had been equilibrated in advance with a 50 mM phosphate buffer (pH 6.8) containing 0.15M sodium chloride. Since albumin does not adsorb to Phenyl Cellulofine® under such conditions, the albumin fractions which passed through the column were collected.

The albumin solution thus recovered was concentrated to a volume of about 50 liters using an ultrafiltration membrane having a molecular weight exclusive limit of 30,000, and at the same time, the buffer in the albumin solution was replaced by a 50 mM phosphate buffer (pH 6.8).

[iv] Anion exchanger treatment

The albumin solution thus treated with hydrophobic chromatography, concentrated and buffer-exchanged in the above step [iii] was applied to a column packed with DEAE-Sepharose® which had been equilibrated in advance with a 50 mM phosphate buffer (pH 6.8). Under such conditions, albumin was not adsorbed to the DEAE-Sepharose® but passed through the column.

[v] Salting-out of HSA

To a 5% HSA solution was added sodium chloride to a final concentration of 1M. The resulting solution was adjusted to pH 3.5 with acetic acid to precipitate HSA, and the thus precipitated HSA was separated from the supernatant fluid by centrifugation, thereby effecting removal of impurities. The albumin precipitate can be used as an injection by dissolving it in a liquid, concentrating and buffer-exchanging the thus dissolved solution using an ultrafiltration membrane having a molecular weight exclusive limit of 30,000, adding a stabilizing agent to the thus treated solution if necessary, and then subjecting the resulting solution to filter sterilization.

[vi] HPLC analysis of purified HSA

The HSA preparation obtained after the purification step by hydrophobic chromatography was analyzed by means of HPLC gel filtration under the following conditions.

(a) Column: TSK gel G3000SWxL® (Tosoh Corp.)

Figure 1A:
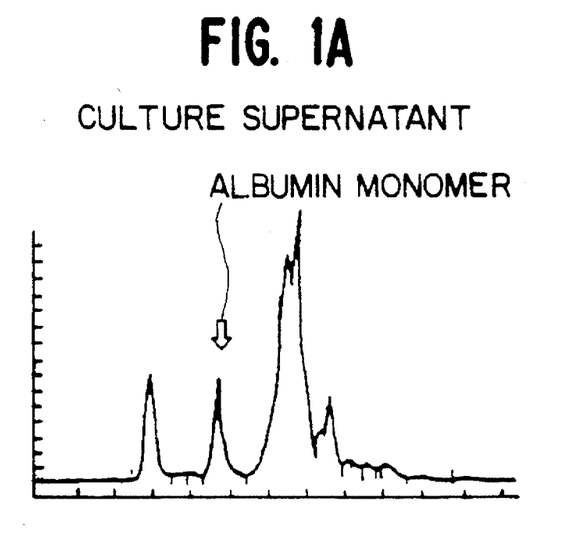
FIG. 1 is a graph showing the results of HPLC analysis of HSA obtained after the hydrophobic chromatography purification step.
Figure 1B:
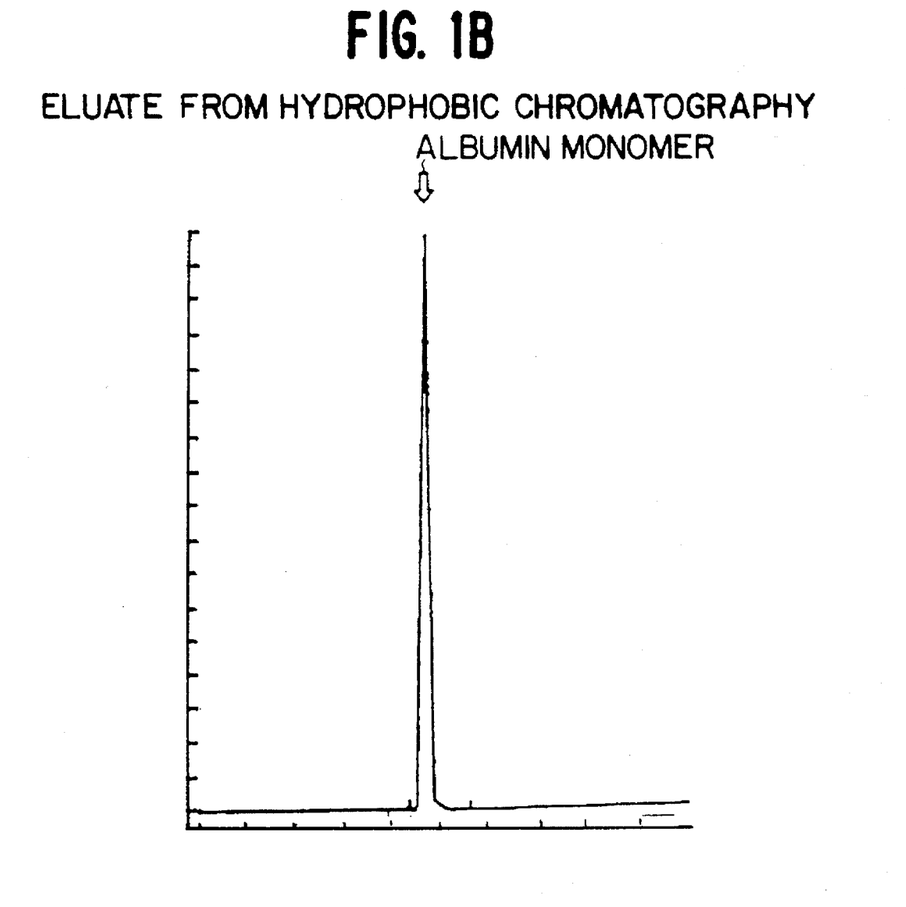

(b) Eluent: 0.3M NaCl/50 mM phosphate buffer (c) Detection: absorbance at 280 nm As shown in FIG. 1, the purified HSA preparation was found as a single peak of HSA monomer.

[vii] Analysis of yeast-derived components

A culture supernatant of a yeast strain which does not produce albumin was partially purified in accordance with the purification process of the instant invention, and separated into a protein fraction and a polysaccharide fraction. Rabbits were immunized with the protein fraction or the polysaccharide fraction. Using an antiserum preparation obtained in that manner, detection of yeast-derived components in the purified albumin solution was carried out by means of enzyme immunoassay (EIA).

Results of the detection of yeast-derived components in a sample obtained after the salting-out step are shown in Table 4. The sample was subjected to the measurement after adjusting the albumin concentration to 250 mg/ml.

Total content of the yeast-derived proteins in the 250 mg/ml albumin solution was found to be 1,360 ng/ml in the case of a sample obtained after treatment by the hydrophobic chromatography and was 5.4 ng/ml in an anion exchanger-treated sample, thus showing reduction of the total content to a level of 1/250 by the latter purification step. In addition, the yeast-derived proteins were not detected in the purified sample obtained after the salting-out step at a detection limit.

[viii] Properties of the purified HSA (1) Molecular weight

Measurement of molecular weight was carried out in accordance with the aforementioned HPLC gel filtration procedure. Molecular weight of the purified HSA of the present invention was found to be about 67,000, which was almost the same as that of the plasma-derived HSA.

(2) Isoelectric point

Isoelectric point was measured by polyacrylamide gel electrophoresis, for example, using phastsystem® (Pharmacia). Isoelectric point of the purified HSA of the present invention was found to be about 4.9, which was almost the same as that of plasma-derived HSA.

(3) Coloring degree

Absorbances at 280 nm, 350 run and 450 nm were measured, and coloring degrees were calculated as an $A_{350}/A_{280}$ ratio and an $A_{450}/A_{280}$ ratio. The $A_{350}/A_{280}$ ratio and the $A_{450}/A_{280}$ ratio of purified HSA of the instant invention were found to be about 0.02 and about 0.01, respectively, which were almost the same as those of plasma-derived HSA.

EXAMPLE 2

The culture broth obtained in Reference Example 2 was treated in the same manner as the procedures described in Example 1. Properties of the thus purified HSA were almost the same as those of the purified HSA disclosed in Example 1, in terms of molecular weight, isoelectric point and coloring degree, as well as polysaccharide content, gel filtration pattern and content of yeast-derived components.

EXAMPLE 3

A 1 ml portion of the 25% solution of purified HSA obtained in Example 1 was mixed with 1 g of DIAION CRB02® (a chelate resin having a styrene-divinylbenzene copolymer as the carrier portion and an N-methylglucamine group as the ligand portion, manufactured by Mitsubishi Kasei Corp.), and the resulting mixture was stirred for 24 hours at room temperature at pH 6.8 and ionic strength of 5 mmho. The resin then was washed with distilled water to recover the non-absorbed fraction. Thereafter, the thus purified HSA was assessed for the properties as set forth in Example 1. Molecular weight, isoelectric point and gel filtration pattern of the thus obtained HSA were the same as those of the HSA obtained in Example 1.

(1) Analysis of yeast-derived components

Results of the detection of yeast-derived components in the 25% HSA solution by EIA, together with the results of Example 1, are shown in Table 4.

TABLE 4

| Results of the detection of yeast-derived components | | |
|---|---|---|
| Sample | Protein content (HSA purity) | Polysaccharide content (HSA purity) |
| Anion exchanger treatment (steps (i) to (iv) of Ex. 1) | 5.4 ng/ml (99.99999784%) | 40 ng/ml |
| Salting-out treatment (steps (i) to (v) of Ex. 1) | <0.1 ng/ml (99.99999996%) | 4 ng/ml (99.9999984%) |
| Steps (i) to (iv) of Ex. 1 and chelate resin treatment | Not measured | 4 ng/ml (99.9999984%) |
| Steps (i) to (v) of Ex. 1 and chelete resin treatment | <0.1 ng/ml (99.99999996%) | <1 ng/ml (99.9999996%) |

(2) Coloring degree

Absorbances at 280 nm, 350 nm, 450 nm and 500 nm were measured, and coloring degrees were calculated as an $A_{350}/A_{280}$ ratio, an $A_{450}/A_{280}$ ratio and an $A_{500}/A_{280}$ ratio. The $A_{350}/A_{280}$ ratio, the $A_{450}/A_{280}$ ratio and the $A_{500}/A_{280}$ ratio of the HSA of the instant invention were found to be about 0.02, about 0.01 and about 0.002, respectively, which were almost the same as those of plasma-derived HSA.

(3) Linked fatty acid content

Measurement was carried out using NFEA-Test Wako® (Wako Pure Chemical Industries, Ltd.). The linked fatty acid content was about 1.6 moles (per mole of HSA) before the chelate resin treatment but was sharply reduced by that treatment to 0.037 mole per mole of HSA.

EXAMPLE 4

The culture broth obtained in Reference Example 2 was treated in the same manner as in Example 1. Properties of the 25% solution of thus purified HSA were almost the same as those disclosed in Examples 1 and 3, in terms of molecular weight, isoelectric point, coloring degree, gel filtration pattern and content of yeast-derived components.

EXAMPLE 5

The 25% solution of the HSA obtained in Example 3 was checked for absorbances at 280 nm and 500 nm. In that case, the coloring degree was calculated as an $A_{500}/A_{280}$ ratio. In addition, other HSA samples were prepared by repeating the process of Example 3, except that DIAION CR20® (Mitsubishi Kasei Corp.) or LEWATIT TP214® (Bayer) was used instead of DIAION CRB02®, and the absorbances were measured to calculate coloring degrees. The results are shown in Table 5. As controls, several HSA samples were prepared using carriers other than the chelate resin of the present invention, as well as other types of cation exchanger, anion exchanger and hydrophobic chromatography carrier, with the results also shown in Table 5.

TABLE 5

| Carrier | Ligand | Resin Trade name | Coloring degree Coloring* |
|---|---|---|---|
| Invention | | | |
| Styrene-divinyl benzene copolymer | N-methylglucamine group | DIAION CRB02 ® (Mitsubishi) | 0.2 |
| Styrene-divinyl benzene copolymer | —NH(CH$_2$CH$_2$NH)$_n$H | DIAION CR20 ® (Mitsubishi) | 0.2 |
| Styrene-divinyl benzene copolymer | —NHCSNH$_2$ | LEWATIT TP214 ® (Bayer) | 0.2 |
| Control | | | |
| Styrene-divinyl benzene copolymer | DEAE | DEAE-Toyopearl ® (Tosoh) | 0.5 |
| Agarose | iminodiacetic acid | Chelating-Sepharose ® (Pharmacia) | 0.8 |
| Anion exchanger | | DEAE Sepharose ® (Pharmacia) | 0.6 |
| Hydrophobic chromatography | | Phenyl Cellulofine ® (Pharmacia) | 0.6 |

Note (*): Coloring degree in an OD$_{500}$/OD$_{280}$ ratio which was defined as 1.0 in the case of the purified HSA obtained through Reference Example 1 and Example 1.

EXAMPLE 6

(Measuring wave length)

Absorbance of the 25% solution of HSA obtained in Example 3 was measured at wave lengths of from 350 nm to 650 nm. Decreasing degrees of absorbance were found. The lowest ratio was found at a wave length of 500 nm. The results are shown in Table 6.

TABLE 6

| Decreasing degree of absorbance | |
|---|---|
| | Decreasing ratio (%) |
| A$_{350}$/A$_{280}$ | 57 |
| A$_{400}$/A$_{280}$ | 37 |
| A$_{450}$/A$_{280}$ | 25 |
| A$_{500}$/A$_{280}$ | 20 |
| A$_{550}$/A$_{280}$ | 34 |
| A$_{600}$/A$_{280}$ | 54 |
| A$_{650}$/A$_{280}$ | 56 |
| | Starting material: 100% |

EXAMPLE 7

The process of Example 3 was repeated except that DIAION CR20® (Mitsubishi Kasei Corp.) was used instead of the chelate resin DIAION CRB02® in the treatment step using 1 ml of the 25% recombinant HSA solution. The DIAION CR20® is a chelate resin having a —NH(CH$_2$CH$_2$NH)$_n$H group as the ligand attached to a styrene-divinylbenzene copolymer carrier. When the thus recovered HSA was checked for linked fatty acids, similar results to those of the case of Example 6 were obtained.

EXAMPLE 8

The process of Example 3 was repeated except that LEWATIT TP214® (Bayer) was used instead of the chelate resin DIAION CRB02® in the treatment step of 1 ml of the 25% recombinant HSA solution. LEWATIT TP214® is a chelate resin having a —NHCSNH$_2$ group as a ligand attached to the styrene-divinylbenzene copolymer carrier. When the thus recovered HSA was checked for linked fatty acids, similar results to those of the case of Example 6 were obtained.

EXAMPLE 9

Purity

Antibodies against the yeast components were prepared to detect impurities of yeast components at a high level of sensitivity. After culturing non-albumin producing yeast, yeast components were partially purified from the culture supernatant and separated into a protein fraction and a polysaccharide fraction. Each fraction was used to immunize rabbits to obtain an antibody against the protein fraction and an antibody against the polysaccharide fraction. An EIA was developed using these antibodies. In EIA system, the detection limit of proteins and polysaccharides were 0.1 ng/ml and 1 ng/ml, respectively. In purified recombinant HSA obtained in Example 3, at a concentration of 250 mg/ml, no yeast components were detected using this EIA system. That is, the contents of yeast-derived proteins and polysaccharides in purified recombinant albumin at a concentration of 25% were less than 0.1 ng/ml and less that 1 ng/ml, respectively. In other words, the purity of recombinant albumin was greater than 99.999999%. Contaminated DNA was assayed by the threshold method as described in Science, 240, 1182 (1988). In purified recombinant albumin, no DNA was detected in a 2 ml extract of a 25% albumin solution. Because the detection limit of this system was 4 pg/2 ml of 25% albumin, the amount of the contaminating DNA was less than that value. Pyrogens were measured using a reagent kit, Endospacy (Seikagaku Corp.). The pyrogen content was less than 0.1 EU/ml of 25% recombinant albumin, a sufficiently low level. In the pyrogen test using rabbits, there was no temperature rise up to a dosage of 2.5 grams per kilogram.

Composition and Structure

To ascertain the composition and structure of recombinant albumin, amino acid analysis was conducted and the CD spectrumwas measured. The amino acid composition and N and C terminal sequence of recombinant albumin were identical to those of plasma albumin. Those results were consistent with the sequence of the c-DNA. Peptide mapping of recombinant albumin was carried out. Albumin was degradated by lysylendopeptiase, then each peptide was separated by reverse-phase HPLC. As a result of comparing the peptide mapping patterns, the elution profile of recombinant albumin was consistent with that of plasma albumin.

To examine the higher structure of recombinant albumin, the CD spectrum of albumin was measured. The CD spectrum of recombinant albumin was identical in the shape and magnitude to that of plasma albumin in the region of 350 nm to 195 nm.

Biological Characterization

One of the most important biological functions of albumin is ligand binding. Albumin binds various materials. The binding abilities of albumin to three typical materials were examined. Bilirubin was selected to represent pigment. Warfarin was used to represent drugs and lauric acid to represent to fatty acids. The binding of those three materials was analyzed using a Scatchard plot model. Binding constants and the number of binding sites of those three materials to recombinant albumin were consistent with those of plasma albumin. Binding curves of lauric acid to albumin are shown in FIG. 2 as an example.

Figure 2:
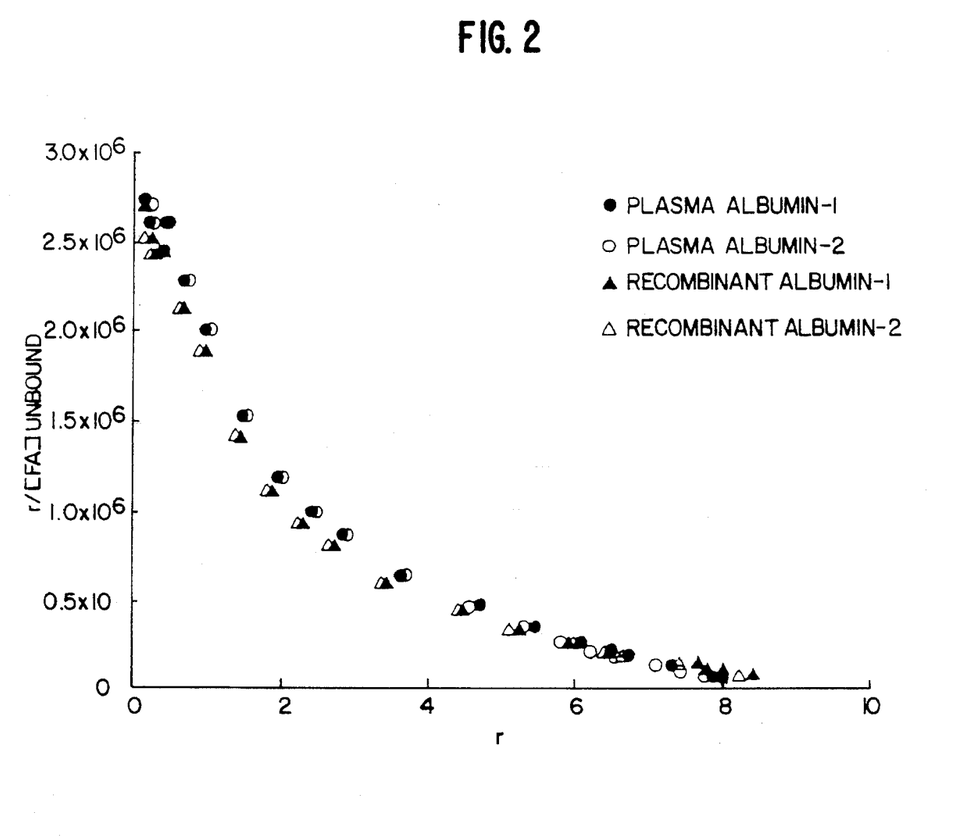
FIG. 2 is a graph showing binding curves of lauric acid to HSA.

As shown in FIG. 2, binding curve of recombinant albumin was consistent with plasma albumin.

The results that binding affinities of recombinant albumin with those ligands were almost similar to those of plasma albumin indicate the biological equivalency between both albumins.

Pre-Clinical Study

Preliminary data was collected during a pre-clinical study conducted in animals. The half life of recombinant albumin in dog blood was almost identical to that of plasma albumin (recombinant albumin; 6.3±0.5 day, plasma albumin; 6.0±0.7 day).

The following hemodynamic parameters were tested in dogs: blood pressure; central venous pressure; pulmonary artery pressure; cardiac output; blood gas; respiration; and electrocardiogram. At doses of 0.5 and 1.5 g/kg, the same results were obtained for recombinant albumin as for plasma albumin.

The results of a pyrogen test using rabbits showed no temperature rise up to a dose of 2.5 g/kg.

An acute toxicity test of recombinant albumin demonstrated no toxicity in monkeys and rats up to a dosage of 12.5 g/kg.

EXAMPLE 10

In an appropriate volume of distilled water for injection were dissolved 5 g of the yeast-derived HSA obtained in Example 1, 107.3 mg of acetyltryptophan sodium salt and 66.5 mg of sodium caprylate to obtain 20 ml of a pharmaceutical preparation containing 25% HSA. The resulting pharmaceutical preparation consisted of 25% HSA, 0.02M acetyltryptophan sodium salt and 0.02M sodium caprylate. The sodium chloride content was found to be 3.7 mg/ml, the pH was 7.0 and the osmotic pressure was about 1, as a ratio against physiologic saline.

EXAMPLE 11

Preservation stability of the HSA-containing pharmaceutical preparation obtained in Example 10 was examined. Determination of dimers (molecular weight distribution) was carried out by gel filtration analysis, coloring degree by absorbance analysis ($A_{350}/A_{280}$) and polymers or decomposed products by electrophoresis (SDS-PAGE). The results are shown in Tables 7 and 8. According to the instant invention, gelation of HSA did not occur. The content of dimers increased gradually when maintained at 40° C., but polymers or decomposed products were not found.

TABLE 7

| Cryopreservation test at −20° C. for 8 weeks (Coloring degree, $A_{350}/A_{280}$) | | | | | |
| --- | --- | --- | --- | --- | --- |
| Sodium acetyl tryptophan (M) | Sodium caprylate (M) | NaCl (mg/ml) | Before preservation | After preservation | Increasing ratio (fold) |
| 0 | 0 | 0 | 0.0236 | 0.0277 | 1.17 |
| 0.02 | 0.02 | 3.7 | 0.0250 | 0.0261 | 1.04 |

| (Dimer content, %) | | | | |
| --- | --- | --- | --- | --- |
| Sodium acetyl tryptophan (M) | Sodium caprylate (M) | NaCl (mg/ml) | Before preservation | After preservation |
| 0 | 0 | 0 | 0.021 | 0.036 |
| 0.02 | 0.02 | 3.7 | 0.021 | 0.020 |

TABLE 8

| Accelerated preservation test at 40° C. for 3 months (Dimer content, %) | | | | |
| --- | --- | --- | --- | --- |
| Sodium acetyl tryptophan (M) | Sodium caprylate (M) | NaCl (mg/ml) | Before preservation | After preservation |
| 0 | 0 | 0 | 0.018 | 0.052 or more |
| 0.02 | 0.02 | 3.7 | 0.018 | 0.036 |

EXAMPLE 12

Sodium chloride was added to the purified HSA obtained in Example 3 (without effecting salting-out [v] in Example 1) to a final concentration of 0.5M. The resulting solution was adjusted to a pH of 3.5 and applied to a column packed with Phenyl-Cellulofine. The column was washed with a 0.5M sodium chloride solution (pH 3.5) and elution was carried out using 50 mM phosphate buffer (pH 6.8) containing 0.15M sodium chloride.

EXAMPLE 13

The HSA concentration of the purified HSA obtained in Example 3 (excluding the salting-out step [v] in Example 1) was adjusted to 2.5 w/v% so that the electric conductivity became 1 mS or below. Calcium tetraborate was added to the resulting solution to a final concentration of 100 mM and a pH value of the solution was adjusted to 9.5. After allowing the solution to stand for 10 hours, the precipitate formed was removed to recover the supernatant which was then concentrated and desalted.

EXAMPLE 14

The purified HSA obtained in Example 13 was treated with a ultrafiltration membrane having a molecular weight exclusive limit of about 100,000.

EXAMPLE 15

The HSA solution was treated in the same manner as in Example 13 except for adding sodium tetraborate to a final concentration of 100 mM in place of calcium tetraborate and adding calcium chloride to a final concentration of 100 mM.

EXAMPLE 16

HSA fractions (run Nos. 1 to 6 shown in Table 9) obtained through tho steps among the steps described in Example 1 shown in Table 9 were examined for the following items. The treatment with a ConA-immobilized carrier was carried out by applying the HSA fraction to a COnA-Sepharose (Pharmacia) column which had been equilibrated with a 50 mM phosphate buffer (pH 6.8) and recovering non-adsorbed fractions.

(1) Determination of the content of free contaminants by the phenol-sulfuric acid method The content of free contaminants in each HSA fraction was determined by the phenol-sulfuric acid method in the conventional manner. Thus, each HSA fraction was directly examined by the phenol-sulfuric acid method to determine the total content of the contaminants (the sum of the free contaminant content and the nonfree contaminant content). Separately, each HSA fraction was treated with ConA-Sepharose (Pharmacia) in the same manner as described above and nonadsorbed fractions containing HSA were subjected to the determination by the phenol-sulfuric acid method to determine the content of nonfree contaminants. A difference obtained by taking the latter from the former means the content of free contaminants. A standard curve was prepared using mannnan as a standard material. The results are shown in Table 9.

TABLE 9

| Run No. | Purification step | | | | | Free contaminant content (µg/250 mg of HSA) |
|---|---|---|---|---|---|---|
| | [i]–[iv] | [v] | [vi] | Example 12 | ConA | |
| 1 | do | — | — | — | — | 1000 |
| 2 | do | do | — | — | — | 500 |
| 3 | do | — | do | — | — | 200 |
| 4 | do | do | do | — | — | <1 |
| 5 | do | do | — | do | — | <1 |
| 6 | do | — | — | — | do | <1 |

Note, [i]–[iv] means the same step from isolation of culture supernatant to anion exchanger treatment as in Example 1.
[v] means the same step of chelate resin treatment as in Example 3.
[vi] means the same step of salting-out in Example 1.
Example 12 means hydrophobic chromatography.

(2) Confirmation of nonantigenicity

The yeast-derived components in the purified HSA solution was determined in the same manner as in Example (vii). As a result, no yeast-derived component higher than the detectable limit of 0.1 ng/ml was detected in the HSA fraction before and after the hydrophobic chromatography according to the present invention.

EXAMPLE 17

The purified HSA (sample 1) obtained in Example 1 (excluding the salting-out step [v]) was adjusted to the HSA concentration of 25 w/v% so that electric conductivity of the solution became 1 mS or less. Calcium tetraborate was added thereto to a final concentration of 100 mM and a pH value was adjusted to 9.5. After allowing the mixture to stand for about 10 hours, the precipitate formed was removed to recover the supernatant which was concentrated and desalted (sample 2). The resulting HSA solution was treated with a ultrafiltration membrane having a molecular weight exclusive limit of 100,000 (sample 3). Samples 1, 2 and 3 were examined for the following items and the results are shown in Table 10.

(1) Recovery of HSA

The HSA content was determined by measuring the absorbance at 280 nm or by performing SDS-PAGE. As a result, recoveries of HSA in samples 2 and 3 were both 95% or more.

(2) Determination of contaminants by EIA

The yeast-derived components were detected in the same manner as in Example 1 (vii). As a result, the content of the contaminants in sample 1 was 10 ng/ml and no contaminant higher that the detectable limit of 0.1 ng/ml was detected in samples 2 and 3.

(3) Determination of free contaminants by the phenol-sulfuric acid method

The content of free contaminants was determined in the same manner as in Example 16 (1).

(4) Determination of pyrogen

The content of pyrogen was determined using Endospecy (Seikagaku Corporation) in accordance with the manufacture's instruction attached to the product.

TABLE 10

| Sample No. | Purification step | HSA recovery | Contaminant content (per 250 mg of HSA) | | Pyrogen (per 250 mg of HSA) |
|---|---|---|---|---|---|
| | | | EIA | Phenol-sulfuric acid method (free) | |
| 1 | After decoloration | — | 10 ng | 700 µg | 2.9 EU |
| 2 | After boric acid salt treatment | ≧95% | <0.1 ng | <1 µg | <0.1 EU |
| 3 | After ultrafiltration | ≧95% | <0.1 ng | <1 µg | <0.1 EU |

While the instant invention has been described in detail and with reference to specific embodiments thereof, it will be apparent to one skilled in the art that various changes and modifications can be made therein without departing from the spirit and scope thereof.

What is claimed is:

1. In a process for purifying a recombinant human serum albumin, the improvement which comprises:
   (1) exposing said albumin to a chelate resin, said chelate resin having an exchange group as a ligand capable of undergoing chelate formation selected from the group consisting of a polyol group, a polyamine group and a thiourea group, and recovering non-adsorbed fractions to yield albumin; and
   (2) carrying out a salt precipitation step of said albumin at a pH of 3 to 5 and a salt concentration of 0.1 to 3M to yield a precipitate of albumin and dissolving said precipitate in a buffer.

2. In a process for purifying a recombinant human serum albumin, the improvement which comprises treating a recombinant human serum albumin with boric acid or a salt thereof to form a percipitate containing contaminants and a supernatant containing the human serum albumin, and recovering the human serum albumin from the supernatant.

3. The process for purifying human serum albumin according to claim 2, further comprising treating the human serum albumin fraction with an ultrafiltration membrane having a molecular weight exclusive limit of 100,000.

4. In a process for purifying a recombinant human serum albumin, the improvement which comprises contacting the recombinant human serum albumin with immobilized ConA and recovering the non-adsorbed fractions to yield albumin.

5. A process for purifying a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of from 3 to 5 to yield an acid-treated sample;

(4) treating the acid-treated sample using an ultrafiltration membrane having a molecular weight exclusive limit of from 100,000 to 500,000 to yield a second filtrate;

(5) exposing the second filtrate to a cation exchanger at a pH of 3 to 5 and a salt concentration of 0.01 to 0.2M, and then exposing said cation exchanger to a pH of 8 to 10 and a salt concentration of 0.2 to 0.5M to yield a first eluate;

(6) allowing the first eluate to contact with a carrier for hydrophobic chromatography at a pH of 6 to 8 and a salt concentration of 0.01 to 0.5M and recovering non-adsorbed fractions to yield a second eluate;

(7) allowing the second eluate to contact with an anion exchanger at a pH of 6 to 8 and a salt concentration of 0.01 to 0.1M, and recovering non-adsorbed fractions to yield said albumin;

(8) exposing said albumin of step (7) to a chelate resin, said chelate resin having an exchange group as a ligand capable of undergoing chelate formation selected from the group consisting of a polyol group, a polyamine group and a thiourea group, and recovering non-adsorbed fractions to yield albumin; and (9) carrying out a salt precipitation step of said albumin of step (8) at a pH of 3 to 5 and a salt concentration of 0.1 to 3M to yield an albumin precipitate and dissolving said precipitate in a buffer.

6. A process for producing a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of from 3 to 5 to yield an acid-treated sample;

(4) treating the acid-treated sample using an ultrafiltration membrane having a molecular weight exclusive limit of from 100,000 to 500,000 to yield a second filtrate;

(5) exposing the second filtrate to a cation exchanger at a pH of 3 to 5 and a salt concentration of 0.01 to 0.2M, and then exposing said cation exchanger to a pH of 8 to 10 and a salt concentration of 0.2 to 0.5M to yield a first eluate;

(6) allowing the first eluate to contact with a carrier for hydrophobic chromatography at a pH of 2 to 5 and a salt concentration of 0.4 to 1M, and exposing the carrier to a pH of 6 to 8 and a salt concentration of 0.01 to 0.3M for yielding a second eluate; and (7) allowing the second eluate to contact with an anion exchanger at a pH of 6 to 8 and a salt concentration of 0.01 to 0.1 M, and recovering non-adsorbed fractions to yield said albumin.

7. A process for producing a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of from 3 to 5 to yield an acid-treated sample;

(4) treating the acid-treated sample using an ultrafiltration membrane having a molecular weight exclusive limit of from 100,000 to 500,000 to yield a second filtrate;

(5) exposing the second filtrate to a cation exchanger at a pH of 3 to 5 and a salt concentration of 0.01 to 0.2M, and then exposing said cation exchanger to a pH of 8 to 10 and a salt concentration of 0.2 to 0.5M to yield a first eluate;

(6) allowing the first eluate to contact with a carrier for hydrophobic chromatography at a pH of 6 to 8 and a salt concentration of 0.01 to 0.5M for yielding a second eluate; and (7) allowing the second eluate to contact with an anion exchanger at a pH of 6 to 8 and a salt concentration of 0.01 to 0.1M, and recovering non-adsorbed fractions to yield said albumin; and (8) contacting said albumin with a carrier for hydrophobic chromatography at a pH of 2 to 5 and a salt concentration of 0.4 to 1M and exposing the carrier to a pH of 6 to 8 and a salt concentration of 0.01 to 0.3M for eluting albumin.

8. A process for producing a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of from 3 to 5 to yield an acid-treated sample;

(4) treating the acid-treated sample using an ultrafiltration membrane having a molecular weight exclusive limit of from 100,000 to 500,000 to yield a second filtrate;

(5) exposing the second filtrate to a cation exchanger at a pH of 3 to 5 and a salt concentration of 0.01 to 0.2M, and then exposing said cation exchanger to a pH of 8 to 10 and a salt concentration of 0.2 to 0.5M to yield a first eluate;

(6) allowing the first eluate to contact with a carrier for hydrophobic chromatography at a pH of 6 to 8 and a salt concentration of 0.01 to 0.5M for yielding a second eluate; and (7) allowing the second eluate to contact with an anion exchanger at a pH of 6 to 8 and a salt concentration of 0.01 to 0.1M, and recovering non-adsorbed fractions to yield said albumin; and (8) treating said albumin with boric acid or a salt thereof to provide an albumin fraction.

9. A process for purifying a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of from 3 to 5 to yield an acid-treated sample;

(4) treating the acid-treated sample using an ultrafiltration membrane having a molecular weight exclusive limit of from 100,000 to 500,000 to yield a second filtrate;

(5) exposing the second filtrate to a cation exchanger at a pH of 3 to 5 and a salt concentration of 0.01 to 0.2M, and then exposing said cation exchanger to a pH of 8 to 10 and a salt concentration of 0.2 to 0.5M to yield a first eluate;

(6) allowing the first eluate to contact with a carrier for hydrophobic chromatography at a pH of 6 to 8 and a salt concentration of 0.01 to 0.5M for yielding a second eluate; and (7) allowing the second eluate to contact with an anion exchanger at a pH of 6 to 8 and a salt concentration of 0.01 to 0.1M, and recovering non-adsorbed fractions to yield said albumin; and (8) contacting said albumin with immobilized ConA and recovering non-adsorbed fractions to yield albumin.

10. A process for purifying a recombinant human serum albumin comprising the steps of:

(1) treating a culture supernatant of a host which expresses human serum albumin, with a first ultrafiltration membrane having a molecular weight exclusive limit of from 100,000 to 500,000 and then with a second ultrafiltration membrane having a molecular weight exclusive limit of from 1,000 to 50,000 to yield a first filtrate;

(2) heat-treating the first filtrate at 50° to 70° C. for 30 minutes to 5 hours to yield a heated sample;

(3) acid-treating the heated sample at a pH of from 3 to 5 to yield an acid-treated sample;

(4) treating the acid-treated sample using an ultrafiltration membrane having a molecular weight exclusive limit of from 100,000 to 500,000 to yield a second filtrate;

(5) exposing the second filtrate to a cation exchanger at a pH of 3 to 5 and a salt concentration of 0.01 to 0.2M, and then exposing said cation exchanger to a pH of 8 to 10 and a salt concentration of 0.2 to 0.5M to yield a first eluate;

(6) allowing the first eluate to contact with a carrier for hydrophobic chromatography at a pH of 6 to 8 and a salt concentration of 0.01 to 0.5M for yielding a second eluate;

(7) allowing the second eluate to contact with an anion exchanger at a pH of 6 to 8 and a salt concentration of 0.01 to 0.1 M, and recovering non-adsorbed fractions to yield said albumin; and (8) exposing said albumin to a chelate resin, said chelate resin having an exchange group as a ligand capable of undergoing chelate formation selected from the group consisting of a polyol group, a polyamine group and a thiourea group, and recovering non-adsorbed fractions to yield albumin;

(9) treating said albumin of step (8) with boric acid or a salt thereof to provide an albumin fraction; and (10) treating said albumin fraction with an ultrafiltration membrane having a molecular weight exclusive limit of 100,000.

* * * * *